United States Patent
Blank et al.

(10) Patent No.: US 6,322,997 B1
(45) Date of Patent: Nov. 27, 2001

(54) PROTEIN RECOVERY

(75) Inventors: Gregory S. Blank, Menlo Park; Daljit S. Narindray, Pleasanton; Gerardo A. Zapata, Foster City, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/460,587

(22) Filed: Dec. 14, 1999

Related U.S. Application Data

(62) Division of application No. 09/097,309, filed on Jun. 12, 1998, now Pat. No. 6,121,428.
(60) Provisional application No. 60/050,951, filed on Jun. 13, 1997.

(51) Int. Cl.$^7$ .............................. C07K 1/34; C07K 16/28; C12P 21/06
(52) U.S. Cl. ..................... 435/68.1; 435/272; 530/387.3; 530/388.22; 530/412; 530/414; 530/417
(58) Field of Search .................................. 435/68.1, 272; 530/387.3, 388.22, 412, 414, 417

(56) References Cited

U.S. PATENT DOCUMENTS

| | | |
|---|---|---|
| 4,007,113 | 2/1977 | Ostreicher . |
| 4,305,782 | 12/1981 | Ostreicher et al. . |
| 4,604,208 | 8/1986 | Chu et al. . |
| 4,676,980 | 6/1987 | Segal et al. . |
| 4,816,567 | 3/1989 | Cabilly et al. . |
| 4,849,352 | 7/1989 | Sullivan et al. . |
| 5,115,101 | 5/1992 | Bloom et al. . |
| 5,429,746 | 7/1995 | Shadle et al. . |
| 5,470,954 | 11/1995 | Neslund et al. . |
| 5,534,615 | 7/1996 | Baker et al. . |
| 5,591,828 | 1/1997 | Bosslet et al. . |
| 6,121,022 | * 9/2000 | Presta et al. ......................... 435/69.7 |

FOREIGN PATENT DOCUMENTS

| | | |
|---|---|---|
| 003089 | 7/1979 | (EP) . |
| 127737 | 12/1984 | (EP) . |
| WO 90/11814 | 10/1990 | (WO) . |
| WO 91/00360 | 1/1991 | (WO) . |
| WO 92/20373 | 11/1992 | (WO) . |
| WO 93/08829 | 5/1993 | (WO) . |
| WO 93/11161 | 6/1993 | (WO) . |
| WO 93/11162 | 6/1993 | (WO) . |
| WO 93/16185 | 8/1993 | (WO) . |
| WO 94/04690 | 3/1994 | (WO) . |
| WO 96/27011 | 9/1996 | (WO) . |

OTHER PUBLICATIONS

Brennan et al., "Preparation of bispecific antibodies by chemical recombination of monoclonal immunoglobulin $G_1$ fragments" *Science* 229:81–83 (Jul. 1985).

(List continued on next page.)

*Primary Examiner*—David Saunders
(74) *Attorney, Agent, or Firm*—Lee K. Tan

(57) ABSTRACT

The invention herein provides a method for recovering a polypeptide comprising exposing a composition comprising a polypeptide to a reagent which binds to, or modifies, the polypeptide, wherein the reagent is immobilized on a solid phase; and then passing the composition through a filter bearing a charge which is opposite to the charge of the reagent in the composition, so as to remove leached reagent from the composition.

7 Claims, 8 Drawing Sheets

OTHER PUBLICATIONS

Bruggemann et al., "Designer Mice: The Production of Human Antibody Repertoires in Transgenic Animals" *Year In Immunology* 7:33–40 (1993).

Carter et al., "High level *escherichia coli* expression and production of a bivalent humanized antibody fragment" *Bio/Technology* 10:163–167 (1992).

Carter et al., "Humanization of an anti-p185$^{HER2}$ antibody for human cancer therapy" *Proc. Natl. Acad. Sci.* 89:4285–4289 (May 1992).

Clackson et al., "Making antibody fragments using phage display libraries" *Nature* 152:624–628 (1991).

Clezardin, "One-step procedure for the rapid isolation of mouse monoclonal antibodies and their antigen binding fragments by fast protein liquid chromatography on a mono Q anion-exchange column" *Journal of Chromatography* 319:67–77 (1985).

Duchosal et al., "Immunization of hu–PBL–SCID mice and the rescue of human monoclonal Fab fragments through combinatorial libraries" *Nature* 355 (6357):258–262 (Jan. 16, 1992).

Gruber et al., "Efficient Tumor Cell Lysis Mediated by a Bispecific Single Chain Antibody Expressed in *Escherichia Coli*" *Journal of Immunology* 152:5368–5374 (1994).

Holliger et al., "Diabodies": Small bivalent and bispecific antibody fragments *Proc. Natl. Acad. Sci. USA* 90:6444–6448 (Jul. 1993).

Jakobovits et al., "Analysis of Homozygous Mutant Chimeric Mice: Deletion of the Immunoglobulin Heavy–Chain Joining Region Blocks B–cell Development and Antibody Production" *Proc. Natl. Acad. Sci. USA* 90:2551–2555 (Mar. 1993).

Jakobovits et al., "Germ–line Transmission and Expression of a Human–Derived Yeast Artificial Chromosome" *Nature* 362:255–258 (Mar. 18, 1993).

Kostelny et al., "Formation of a Bispecific Antibody by the Use of Leucine Zippers" *Journal of Immunology* 148(5):1547–1553 (1992).

Landschulz et al., "The Leucine Zipper: A Hypothetical Structure Common to a New Class of DNA Binding Proteins" *Science* 240:1759–1764 (1988).

Lindmark et al., "Binding of immunoglobulins to protein A and immunoglobulin levels in mammalian sera" *J. Immunol. Meth.* 62:1–13 (1983).

Marks et al., "By–passing immunization: building high affinity human antibodies by chain shuffling" *Bio/Technology* 10:779–783 (1992).

Marks et al., "By–passing immunization: human antibodies from V–gene libraries displayed on phage" *J. Mol. Biol.* 222:581–597 (1991).

McCafferty et al., "Phage antibodies: filamentous phage displaying antibody variable domains" *Nature* 348:552–554 (1990).

Milstein et al., "Hybrid Hybridomas and Their Use in Immunohistochemistry" *Nature* 305:537–540 (1983).

Morimoto et al., "Single–step purification of F(ab')$_2$ fragments of mouse monoclonal antibodies (immunoglobulins G1) by hydrophobic interaction high performance liquid chromatography using TSKgel Phenyl–5PW" *Journal of Biochemical and Biophysical Methods* 24:107–117 (1992).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

O'Shea et al., "Preferential heterodimer formation by isolated leucine zippers from fos and jun" *Science* 245(4918):646–648 (Aug. 11, 1989).

Pluckthun, "Antibodies from *Escherichia coli*" *The Pharmacology of Monoclonal Antibodies,* Rosenburg and Moore, New York:Springer–Verlag, Chapter 11, vol. 113:269–315 (1994).

Presta et al., "Humanization of an Antibody Directed Against IgE" *J. Immunol.* 151(5):2623–2632 (Sep. 1, 1993).

Reif et al., "Characterization and application of strong ion–exchange membrane adsorbers as stationary phases in high–performance liquid chromatography of proteins" *Journal of Chromatography A* 654:29–41 (1993).

Sahni et al., "Photosynthetic activity of immobilized *Staphylococcus aureus* V8 protease: application in the semisynthesis of molecular variants of α–globin" *Analytical Biochemistry* 193(2):178–185 (Mar. 2, 1991).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217–225 (Jan. 1, 1992).

Suresh et al., "Bispecific Monoclonal Antibodies from Hybrid Hybridomas" *Methods in Enzymology* 121:210–228 (1986).

Traunecker et al., "Bispecific Single Chain Molecules (Janusins) Target Cytotoxic Lymphocytes on HIV Infected cells" *EMBO Journal* 10(12):3655–3659 (1991).

Tutt et al., "Trispecific F(ab')$_3$ Derivatives that Use Cooperative Signaling Via the TCR/CD3 Complex and CD2 to Activate and Redirect Resting Cytotoxic T Cells" *J. Immunol.* 147(1):60–69 (1991).

Voyksner et al., "Optimization of immobilized enzyme hydrolysis combined with high–performance liquid chromatography/thermospray mass spectrometry for the determination of neuropeptides" *Analytical Biochemistry* 188(1):72–81 (Jul. 1990).

Waterhouse et al., "Combinatorial infection and in vivo recombination: a strategy for making large phage antibody repertoires" *Nucleic Acids Research* 21:2265–2266 (1993).

Zapata et al., "Engineering linear F(ab')$_2$ fragments for efficient production in *Escherichia coli* and enhanced antiproliferative activity" *Protein Engineering* 8(10):1057–1062 (1995).

\* cited by examiner

EVQLVESGGGLVQPGGSLRLSCATSGYTFTEYTMHWMRQAPGKGLEWVAGINPKNG
GTSHNQRFMDRFTISVDKSTSTAYMQMNSLRAEDTAVYYCARWRGLNYGFDVRYFD
VWGQGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDK
THTCPPCPAPELLGGRMKQLEDKVEELLSKNYHLENEVARLKKLVGER

FIG. 1A

DIQMTQSPSSLSASVGDRVTITCRASQDINNYLNWYQQKPGKAPKLLIYYTSTLHSGVP
SRFSGSGSGTDYLTISSLQPEDFATYCQQGNTLPPTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

FIG. 1B

Intact Ab    F(ab')₂    Fab'    Light Chain    Fd' (Heavy Chain)

Fc rhuMAbCD18 precursor →(Pepsin cleavage)→ rhuMAbCD18

```
  1 GAATTCAACT TCTCCATACT TTGGATAAGG AAATACAGAC ATGAAAAATC TCATTGCTGA

61 GTTGTTATTT AAGCTTTGGA GATTATCGTC ACTGCAATGC TTCGCAATAT GGCGCAAAAT

121 GACCAACAGC GGTTGATTGA TCAGGTAGAG GGGGCGCTGT ACGAGGTAAA GCCCGATGCC

181 AGCATTCCTG ACGACGATAC GGAGCTGCTG CGCGATTACG TAAAGAAGTT ATTGAAGCAT

241 CCTCGTCAGT AAAAAGTTAA TCTTTTCAAC AGCTGTCATA AAGTTGTCAC GGCCGAGACT

301 TATAGTCGCT TTGTTTTTAT TTTTTAATGT ATTTGTAACT AGAATTCGAG CTCGCCGGGG

361 ATCCTCTAGA GGTTGAGGTG ATTTT ATG AAA AAG AAT ATC GCA TTT CTT CTT
-23                                M   K   K   N   I   A   F   L   L

413 GCA TCT ATG TTC GTT TTT TCT ATT GCT ACA AAC GCG TAC GCT GAT ATC
-14 A   S   M   F   V   F   S   I   A   T   N   A   Y   A   D   I

461 CAG ATG ACC CAG TCC CCG AGC TCC CTG TCC GCC TCT GTG GGC GAT AGG
  3 Q   M   T   Q   S   P   S   S   L   S   A   S   V   G   D   R

509 GTC ACC ATC ACC TGT CGT GCC AGT CAG GAC ATC AAC AAT TAT CTG AAC
 19 V   T   I   T   C   R   A   S   Q   D   I   N   N   Y   L   N

557 TGG TAT CAA CAG AAA CCA GGA AAA GCT CCG AAA CTA CTG ATT TAC TAT
 35 W   Y   Q   Q   K   P   G   K   A   P   K   L   L   I   Y   Y

605 ACC TCC ACC CTC CAC TCT GGA GTC CCT TCT CGC TTC TCT GGT TCT GGT
 51 T   S   T   L   H   S   G   V   P   S   R   F   S   G   S   G

653 TCT GGG ACG GAT TAC ACT CTG ACC ATC AGC AGT CTG CAA CCG GAG GAC
 67 S   G   T   D   Y   T   L   T   I   S   S   L   Q   P   E   D

701 TTC GCA ACT TAT TAC TGT CAG CAA GGT AAT ACT CTG CCG CCG ACG TTC
 83 F   A   T   Y   Y   C   Q   Q   G   N   T   L   P   P   T   F

749 GGA CAG GGC ACG AAG GTG GAG ATC AAA CGA ACT GTG GCT GCA CCA TCT
 99 G   Q   G   T   K   V   E   I   K   R   T   V   A   A   P   S

797 GTC TTC ATC TTC CCG CCA TCT GAT GAG CAG TTG AAA TCT GGA ACT GCC
115 V   F   I   F   P   P   S   D   E   Q   L   K   S   G   T   A

845 TCT GTT GTG TGC CTG CTG AAT AAC TTC TAT CCC AGA GAG GCC AAA GTA
131 S   V   V   C   L   L   N   N   F   Y   P   R   E   A   K   V

893 CAG TGG AAG GTG GAT AAC GCC CTC CAA TCG GGT AAC TCC CAG GAG AGT
147 Q   W   K   V   D   N   A   L   Q   S   G   N   S   Q   E   S

941 GTC ACA GAG CAG GAC AGC AAG GAC AGC ACC TAC AGC CTC AGC AGC ACC
163 V   T   E   Q   D   S   K   D   S   T   Y   S   L   S   S   T

989 CTG ACG CTG AGC AAA GCA GAC TAC GAG AAA CAC AAA GTC TAC GCC TGC
179 L   T   L   S   K   A   D   Y   E   K   H   K   V   Y   A   C

1037 GAA GTC ACC CAT CAG GGC CTG AGC TCG CCC GTC ACA AAG AGC TTC AAC
195  E   V   T   H   Q   G   L   S   S   P   V   T   K   S   F   N

1085 AGG GGA GAG TGT TAA G CTGATCCTCT ACGCCGGACG CATCGTGGCG
211  R   G   E   C
```

FIG. 4A

```
1131 CTAGTACGCA AGTTCACGTA AAAACGGTAT CTAGAGGTTG AGGTGATTTT     ATG AAA
 -23                                                            M   K

1187 AAG AAT ATC GCA TTT CTT CTT GCA TCT ATG TTC GTT TTT TCT ATT GCT
 -21  K   N   I   A   F   L   L   A   S   M   F   V   F   S   I   A

1235 ACA AAC GCG TAC GCT GAG GTT CAG CTG GTG GAG TCT GGC GGT GGC CTG
  -5  T   N   A   Y   A   E   V   Q   L   V   E   S   G   G   G   L

1283 GTG CAG CCA GGG GGC TCA CTC CGT TTG TCC TGT GCA ACT TCT GGC TAC
  12  V   Q   P   G   G   S   L   R   L   S   C   A   T   S   G   Y

1331 ACC TTT ACC GAA TAC ACT ATG CAC TGG ATG CGT CAG GCC CCG GGT AAG
  28  T   F   T   E   Y   T   M   H   W   M   R   Q   A   P   G   K

1379 GGC CTG GAA TGG GTT GCA GGG ATT AAT CCT AAA AAC GGT GGT ACC AGC
  44  G   L   E   W   V   A   G   I   N   P   K   N   G   G   T   S

1427 CAC AAC CAG AGG TTC ATG GAC CGT TTC ACT ATA AGC GTA GAT AAA TCC
  60  H   N   Q   R   F   M   D   R   F   T   I   S   V   D   K   S

1475 ACC AGT ACA GCC TAC ATG CAA ATG AAC AGC CTG CGT GCT GAG GAC ACT
  76  T   S   T   A   Y   M   Q   M   N   S   L   R   A   E   D   T

1523 GCC GTC TAT TAT TGT GCT AGA TGG CGA GGC CTG AAC TAC GGC TTT GAC
  92  A   V   Y   Y   C   A   R   W   R   G   L   N   Y   G   F   D

1571 GTC CGT TAT TTT GAC GTC TGG GGT CAA GGA ACC CTG GTC ACC GTC TCC
 108  V   R   Y   F   D   V   W   G   Q   G   T   L   V   T   V   S

1619 TCG GCC TCC ACC AAG GGC CCA TCG GTC TTC CCC CTG GCA CCC TCC TCC
 124  S   A   S   T   K   G   P   S   V   F   P   L   A   P   S   S

1667 AAG AGC ACC TCT GGG GGC ACA GCG GCC CTG GGC TGC CTG GTC AAG GAC
 140  K   S   T   S   G   G   T   A   A   L   G   C   L   V   K   D

1715 TAC TTC CCC GAA CCG GTG ACG GTG TCG TGG AAC TCA GGC GCC CTG ACC
 156  Y   F   P   E   P   V   T   V   S   W   N   S   G   A   L   T

1763 AGC GGC GTG CAC ACC TTC CCG GCT GTC CTA CAG TCC TCA GGA CTC TAC
 172  S   G   V   H   T   F   P   A   V   L   Q   S   S   G   L   Y

1811 TCC CTC AGC AGC GTG GTG ACC GTG CCC TCC AGC AGC TTG GGC ACC CAG
 188  S   L   S   S   V   V   T   V   P   S   S   S   L   G   T   Q

1859 ACC TAC ATC TGC AAC GTG AAT CAC AAG CCC AGC AAC ACC AAG GTC GAC
 204  T   Y   I   C   N   V   N   H   K   P   S   N   T   K   V   D

1907 AAG AAA GTT GAG CCC AAA TCT TGT GAC AAA ACT CAC ACA TGC CCG CCG
 220  K   K   V   E   P   K   S   C   D   K   T   H   T   C   P   P

1955 TGC CCA GCA CCA GAA CTG CTG GGC GGC CGC ATG AAA CAG CTA GAG GAC
 236  C   P   A   P   E   L   L   G   G   R   M   K   Q   L   E   D

2003 AAG GTC GAA GAG CTA CTC TCC AAG AAC TAC CAC CTA GAG AAT GAA GTG
 252  K   V   E   E   L   L   S   K   N   Y   H   L   E   N   E   V

2051 GCA AGA CTC AAA AAG CTT GTC GGG GAG CGC TAA     GCATGCG ACGGCCCTAG
 268  A   R   L   K   K   L   V   G   E   R

2101 AGTCCCTAAC GCTCGGTTGC CGCCGGGCGT TTTTTATTGT TAA
```

FIG. 4B

| Strain | Genotype |
|---|---|
| W3110 | K-12 F⁻ lambda⁻ IN*rrnD-rrnE1* |
| ↓ | |
| 1A2 | W3110 Δ*fhuA* |
| ↓ | |
| 7C1 | W3110 Δ*fhuA* Δ*phoA* Δ(*argF-lac*) |
| ↓ | |
| 16C9 | W3110 Δ*fhuA* Δ*phoA* Δ(*argF-lac*) *deoC* |
| ↓ | |
| 23E3 | W3110 Δ*fhuA* Δ*phoA* Δ(*argF-lac*) *deoC* Δ*degP* |
| ↓ | |
| 33B6 | W3110 Δ*fhuA* Δ*phoA* Δ(*argF-lac*) *deoC* Δ*degP ilvG* |
| ↓ | |
| 49B2 | W3110 Δ*fhuA* Δ*phoA* Δ(*argF-lac*) *deoC* Δ*degP ilvG* Δ*fucP* |
| ↓ | |
| 49A5 | W3110 Δ*fhuA* Δ*phoA* Δ(*argF-lac*) *deoC* Δ*degP ilvG* Δ*fucP* Δ*malE* |

FIG. 5

PROTEIN RECOVERY

RELATED APPLICATIONS

This is a divisional application claiming priority under 35 U.S.C. §120 to co-pending application Ser. No. 09/097,309 filed on Jun. 12, 1998 (U.S. Pat. No. 6,121,428) which is a non-provisional application filed under 37 CFR 1.53(b)(1), claiming priority under 35 USC 119(e) to provisional application No. 60/050,951 filed Jun. 13, 1997, the contents of which are incorporated herein by reference.

BACKGROUND OF THE INVENTION

1. Field of the Invention

This invention relates generally to protein recovery. In particular, it pertains to recovery of a polypeptide, wherein the polypeptide is exposed to an immobilized reagent which binds to, or modifies, the polypeptide.

2. Description of Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, Its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

As part of the overall recovery process for the protein, the protein may be exposed to an immobilized reagent which binds to or modifies the protein. For example, the protein may be subjected to affinity chromatography wherein an immobilized reagent which binds specifically to the protein, such as an antibody, captures the antibody and impurities pass through the affinity chromatography column. The protein can be subsequently eluted from the column by changing the conditions such that the protein no longer binds to the immobilized reagent. The immobilized reagent may also be an enzyme which modifies the protein. Sahni et al., *Anal. Biochem.* 193:178–185 (1991) and Voyksner et al, *Anal. Biochem.* 188:72–81 (1990) describe immobilized proteases.

Another type of purification process is filtration. Filtration of fine particle size contaminants from fluids has been accomplished by the use of various porous filter media through which a contaminated composition is passed such that the filter retains the contaminant. Retention of the contaminant may occur by mechanical straining or electrokinetic particle capture and adsorption. In mechanical straining, a particle is retained by physical entrapment when it attempts to pass through a pore smaller than itself. In the case of electrokinetic capture mechanisms, the particle collides with a surface within the porous filter and is retained on the surface by short range attractive forces. To achieve electrokinetic capture, charge modifying systems can be used to alter the surface charge characteristics of a filter (see, e.g., WO90/11814). For example, where the contaminant to be removed is anionic, a cationic charge modifier can be used to alter the charge characteristics of the filter such that the contaminant is retained by the filter.

There is a need in the art for improved methods for recovering polypeptides, especially those polypeptides produced by recombinant techniques.

SUMMARY OF THE INVENTION

Accordingly, the invention provides a method for recovering a polypeptide comprising: (a) exposing a composition comprising a polypeptide to a reagent which binds to, or modifies, the polypeptide, wherein the reagent is immobilized on a solid phase; and then (b) passing the composition through a filter bearing a charge which is opposite to the charge of the reagent in the composition, so as to remove leached reagent from the composition. Preferably the charge characteristics of the polypeptide in the composition in step (b) are such that the polypeptide passes through the filter and preferably the filter is placed in line with the composition exposed to the reagent as in step (a). In one embodiment of the invention, the polypeptide to be treated in step (a) is a precursor polypeptide and the immobilized reagent is a protease (e.g. pepsin) which removes a precursor domain (e.g. a leucine zipper dimerization domain) from the polypeptide.

The invention also provides a method for recovering a polypeptide comprising removing a leached reagent from a composition comprising the polypeptide and the leached reagent by passing the composition through a filter bearing a charge opposite to that of the leached reagent, wherein the leached reagent was previously immobilized on a solid phase.

In yet a further embodiment, the invention provides a method for modifying a precursor antibody comprising a leucine zipper dimerization domain, comprising exposing the precursor antibody to a protease immobilized on a solid phase such that the protease removes the leucine zipper from the precursor antibody. This method optionally further comprises passing the antibody free of the leucine zipper through a positively charged filter placed in line with antibody which has been exposed to the immobilized protease.

The anti-CD18 purification process is an example of a process in which an immobilized reagent is required to remove a leucine zipper dimerization domain from the anti-CD18 antibody precursor. The antibody precursor is initially purified using ABX cation exchange chromatography before the leucine zipper domain is removed by digestion with pepsin. The amount of pepsin necessary to completely remove the leucine zipper from the antibody precursor is considerable. A ratio of 1 mg of pepsin per 20 mg of antibody is necessary to carry out the digestion over a reasonable period of time. Treatment like this will leave a large amount of pepsin to be removed in the remaining steps of the anti-CD18 purification process (FIG. 7). Quick removal of pepsin was found to be beneficial, since excessive exposure to pepsin resulted in overdigestion of the anti-CD18 antibody, with significant loses of intact product. In order to effectively control the amount of pepsin added to the anti-CD18 precursor antibody, and effectively eliminate any traces of pepsin that can persist through the purification process, two methods were implemented into the anti-CD18 antibody purification process. First, to considerably reduce the amount of pepsin added to the ABX purified antibody precursor pool, pepsin was immobilized on a solid phase (i.e. coupled to control pore glass beads (CPG) and packed into a column). The digestion reaction was then carried out by flowing the antibody precursor pool through the pepsin-CPG column. This procedure limited the amount of pepsin added into the antibody precursor pool. Nevertheless, a further problem was identified in that pepsin was found to leach from the solid phase. A small amount of pepsin leaching from the solid phase was found to be sufficient to cause overdigestion of the anti-CD18 antibody, resulting in a reduction in product yields. To overcome this problem of pepsin leaching from the solid phase, a positively charged filter was placed in line with the effluent from the pepsin-CPG column. The filter was found to remove all pepsin leaching from the solid phase, thereby preventing overdigestion of the antibody precursor. Pepsin is an acidic protein with a low pI. Therefore at pH 4, the pH of the digestion step, pepsin remained negatively charged and bound strongly to the positively charged filter. The use of a charged filter instead of a resin to remove leachables was found to be advantageous, since filters are compact and capable of very high flow rates with minimal backpressure. A filter can be implemented in line without the need to perform a separate recovery step, therefore reducing process complexity and time.

It is envisaged that negatively and positively charged filters can be used to solve problems associated with leaching of formerly immobilized reagents in other recovery processes.

BRIEF DESCRIPTION OF THE DRAWINGS

FIGS. 1A and 1B depict the amino acid sequence of rhuMAb CD18 heavy chain (FIG. 1A; SEQ ID NO:1) and light chain (FIG. 1B; SEQ ID NO:2). The sequence in italics in FIG. 1A (SEQ ID NO:3) is that of the leucine zipper.

FIG. 2B shows pepsin cleavage of the rhuMAb CD18 precursor to yield rhuMAb CD18, free of the leucine zipper.

FIGS. 4A and 4B depict the full sequence of the pS1130 expression cassette (SEQ ID NO:5).

FIG. 5 shows derivation of the 49A5 production cell line.

DETAILED DESCRIPTION OF THE PREFERRED EMBODIMENTS

Definitions

Figure 2A:
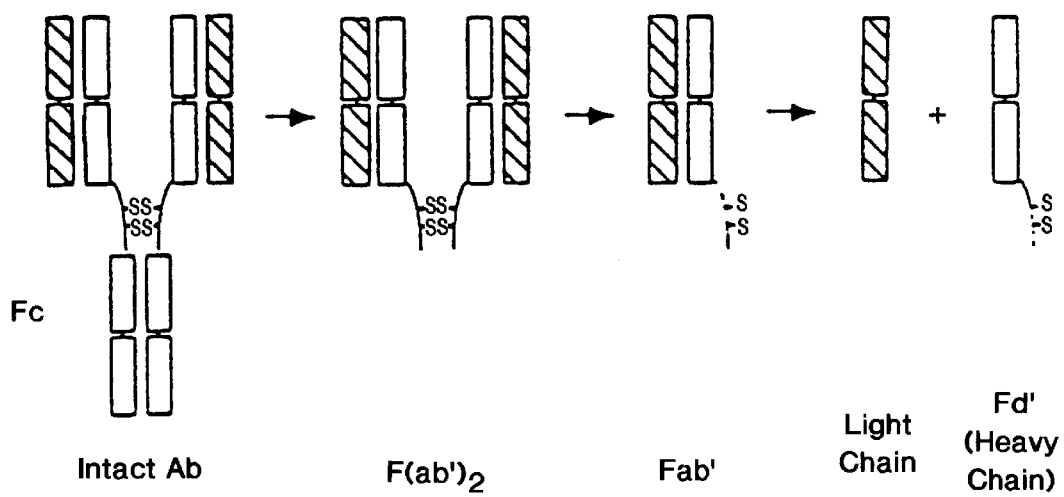
FIGS. 2A and 2B depict intact antibody (Ab) and a variety of antibody fragments (F(ab')$_2$, Fab', light chain and Fd'). Heavy chains are depicted in white and light chains are hatched. The two disulfide bonds that form between two heavy chains are shown as -ss-.

As used herein, "polypeptide" refers generally to peptides and proteins having more than about ten amino acids. Preferably, the polypeptide is a mammalian protein, examples of which include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides.

A "variant" or "amino acid sequence variant" of a starting polypeptide is a polypeptide that comprises an amino acid sequence different from that of the starting polypeptide.

Generally, a variant will possess at least 80% sequence identity, preferably at least 90% sequence identity, more preferably at least 95% sequence identity, and most preferably at least 98% sequence identity with the native polypeptide. Percentage sequence identity is determined, for example, by the Fitch et al., *Proc. Natl. Acad. Sci. USA* 80:1382–1386 (1983), version of the algorithm described by Needleman et al., *J. Mol. Biol.* 48:443–453 (1970), after aligning the sequences to provide for maximum homology. Amino acid sequence variants of a polypeptide are prepared by introducing appropriate nucleotide changes into DNA encoding the polypeptide, or by peptide synthesis. Such variants include, for example, deletions from, and/or insertions into and/or substitutions of, residues within the amino acid sequence of the polypeptide of interest. Any combination of deletion, insertion, and substitution is made to arrive at the final construct, provided that the final construct possesses the desired characteristics. The amino acid changes also may alter post-translational processes of the polypeptide, such as changing the number or position of glycosylation sites. Methods for generating amino acid sequence variants of polypeptides are described in U.S. Pat No. 5,534,615, expressly incorporated herein by reference, for example.

In preferred embodiments of the invention, the polypeptide is a recombinant polypeptide. A "recombinant polypeptide" is one which has been produced in a host cell which has been transformed or transfected with nucleic acid encoding the polypeptide, or produces the polypeptide as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well a cell within a host animal. Methods for recombinant production of polypeptides are described in U.S. Pat. No. 5,534,615, expressly incorporated herein by reference, for example.

A "precursor polypeptide" herein is a polypeptide to which is fused one or more precursor domains, e.g. where the precursor domain is part of a polypeptide chain of the polypeptide or is covalently attached to the polypeptide by a chemical linker, for example. The "precursor domain" may be an amino acid residue or polypeptide. For example, the precursor domain may be a dimerization domain such as a leucine zipper, an amino acid sequence such as polyglutamic acid which bears a negative charge and another amino acid sequence such as polylysine which bears a positive charge, or a peptide helix bundle comprising a helix, a turn and another helix; an epitope tag useful, e.g., in purification of the polypeptide of interest; an amino acid residue or peptide at the amino or carboxy terminus of the polypeptide which is desired to be removed to generate a homogenous polypeptide preparation; a N-terminal methionine, an artifact of production of the polypeptide in recombinant cell culture; a pre, pro or prepro domain of a mature polypeptide (e.g. the pro domain of prothrombin, wherein removal of the pro domain generates the biologically active mature thrombin molecule); a polylysine polypeptide; an enzyme such as glutathione transferase; or the Fc region of an intact antibody which is removed to generate an $F(ab')_2$.

An "epitope tag" polypeptide has enough residues to provide an epitope against which an antibody thereagainst can be made, yet is short enough such that it does not interfere with activity of the polypeptide to which it is fused. The epitope tag preferably is sufficiently unique so that the antibody thereagainst does not substantially cross-react with other epitopes. Suitable epitope tag polypeptides generally have at least 6 amino acid residues and usually between about 8–50 amino acid residues (preferably between about 9–30 residues). Examples include the flu HA tag polypeptide and its antibody 12CA5 (Field et al. *Mol. Cell. Biol.* 8:2159–2165 (1988)); the c-myc tag and the 8F9, 3C7, 6E10, G4, B7 an 9E10 antibodies thereto (Evan et al., *Mol. Cell. Biol.* 5(12):3610–3616 (1985)); and the Herpes Simplex virus glycoprotein D (gD) tag and its antibody (Paborsky et al., *Protein Engineering* 3(6):547–553 (1990)).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those polypeptides discussed above. Preferred molecular targets for antibodies encompassed by the present invention include CD polypeptides such as CD3, CD4, CD8, CD19, CD20 and CD34; members of the ErbB receptor family such as the EGF receptor, HER2, HER3 or HER4 receptor; cell adhesion molecules such as LFA-1, Mac1, p150,95, VLA-4, ICAM-1, VCAM and $\alpha v/\beta 3$ integrin including either $\alpha$ or $\beta$ subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., *Nature,* 348:552–554 (1990). Clackson et al., *Nature,* 352:624–628 (1991) and Marks et al., *J. Mol. Biol.,* 222:581–597 (1991) describe the isolation of murine and human antibodies, respectively, using phage libraries. Subsequent publications describe the production of high affinity (nM range) human antibodies by chain shuffling (Marks et al., *Bio/Technology,* 10:779–783 (1992)), as well as combinatorial infection and in vivo recombination as a strategy for constructing very large phage libraries (Waterhouse et al., *Nuc. Acids. Res.,* 21:2265–2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255–258 (1993); Bruggemann et al., *Year in Immuno.,* 7:33 (1993); and Duchosal et al. *Nature* 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851–6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Polypeptides of Immunological Interest,* 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk *J. Mol. Biol.* 196:901–917 (1987)). "Framework" or "FR" residues are those variable domain residues other than the hypervariable region residues as herein defined. The CDR and FR residues of the H52 antibody of the example below are identified in Eigenbrot et al. *Polypeptides: Structure, Function and Genetics* 18:49–62 (1994).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immnol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

In a preferred embodiment of the invention, the antibody is an antibody fragment which is preferably human or humanized (see above discussion concerning humanized antibodies).

"Antibody fragments" comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163–167 (1992)). In another embodiment as described in the Example below, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies,* vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., *Proc. Natl. Acad. Sci. USA* 90:6444–6448 (1993).

The expression "linear antibodies" when used throughout this application refers to the antibodies described in Zapata et al. *Polypeptide Eng.* 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptorCD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER\ 2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Milstein et al., *Nature,* 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/20372, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217–225 (1992) describe the production of a fully humanized bispecific antibody $F(ab')_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.,* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al *J. Immunol.* 147: 60 (1991).

By "recovering a polypeptide" is meant obtaining a polypeptide preparation from a "pre-recovery preparation" by purifying the pre-recovery preparation (see below) or by modifying a precursor polypeptide to generate a form of the polypeptide which is free of the precursor domain.

By "purifying" a composition comprising an polypeptide and one or more contaminants is meant increasing the degree of purity of the polypeptide in the composition by removing (completely or partially) at least one contaminant from the composition. A "purification step" may be part of an overall purification process resulting in an "essentially pure" composition, which is used herein to refer to a composition comprising at least about 90% by weight of the polypeptide of interest, based on total weight of the composition, preferably at least about 95% by weight. "Essentially homogeneous" herein refers to a composition comprising at least about 99% by weight of polypeptide of interest, based on total weight of the composition.

The "reagent" of interest herein is a compound or composition (preferably a polypeptide) which is able to bind to and/or modify a polypeptide of interest. A "leached" reagent is one which has come free from the solid phase. The reagent may, for example, bind to the polypeptide as is the case for "capture reagents" used in affinity purification methods. Examples of such "capture reagents" include protein A or protein G for capturing polypeptides such as antibodies and immunoadhesins; antibodies which can be used for affinity purification of polypeptides; a ligand binding domain of a receptor for capturing a ligand thereto; a receptor binding domain for capturing a receptor or a fragment thereof binding protein (e.g. IGFBPs such as IGFBP-3 and growth hormone binding proteins (GHBPs)); and immunoadhesins. Alternatively, or in addition, the reagent may modify the polypeptide of interest. For example, the reagent may chemically or physically alter the polypeptide. By "chemical alteration" is meant modification of the polypeptide by, e.g., bond formation or cleavage resulting in a new chemical entity. By "physical alteration" is meant changes in the higher order structure of the polypeptide. Enzymes are examples of reagents which can chemically and/or physically modify the polypeptide. The preferred enzyme is a protease (e.g. for removing one or more precursor domains from a precursor polypeptide). A "protease" is an enzyme which can hydrolyze a polypeptide. Examples of proteases include pepsin, cathepsin, trypsin, papain, elastase, carboxypeptidases, aminopeptidases, subtilisin, chymotrypsin, thermolysin, $V_8$ protease, prolinase and other endo- or exopeptidases.

By "solid phase" is meant a non-aqueous matrix to which a reagent can adhere. The solid phase may be a purification column, a discontinuous phase of discrete particles, a membrane or filter. Examples of materials for forming the solid phase include polysaccharides (such as agarose and cellulose); and other mechanically stable matrices such as silica (e.g. controlled pore glass), poly(styrenedivinyl) benzene, polyacrylamide, ceramic particles and derivatives of any of the above. In preferred embodiments, the solid phase comprises controlled pore glass beads retained in a column. In certain embodiments, the solid phase is coated with a reagent (such as glycerol) which is intended to prevent nonspecific adherence of contaminants to the solid phase.

The reagent discussed above may be "immobilized" on or in the solid phase by forming a covalent bond between a functional group of the reagent and a reactive group on the surface of the solid phase. In other embodiments, the reagent is "immobilized" on the solid phase by adsorption and ionic binding or may be entrapped in the solid phase, e.g., within cells or lattice type polymers or microcapsules (See Holenberg and Roberts in *Enzymes as Drugs* John Wiley & Sons NY (1981), pages 396–411). The reagent should essentially retain its ability to bind to and/or modify the polypeptide of interest once immobilized to the solid phase. Reagent immobilization may be achieved by matrix activation. Briefly, this generally involves first activating the solid phase by a specific chemical reaction depending on the surface chemistry and then immobilizing the reagent by combining it with the activated solid phase. Activation of the solid phase can involve activation of hydroxyl groups (e.g. cyanogen bromide activation of the solid phase); carboxyl groups (e.g. using N-hydroxybenzotriazole in the presence of a water-soluble carbodiimide); acyl hydrazide (using, e.g., glutaraldehyde to generate aldehyde groups); amines (using, e.g., nitrous acid, phosgene and thiosphosgene, or cyanogen bromide); or acrylonitrile. In another embodiment, the reagent may be immobilized using a cross-linking agent (i.e. the reagent is immobilized indirectly to the solid phase) such as zero-length cross-linkers (e.g. carbodiimide, Woodward's reagent K, chloroformates and carbonyldiimidazole); homobifunctional cross-linkers (e.g. glutaraldehyde, chloroformates and carbonyldiimidazole, heterocyclic halides, divinylsulfone, quinones and transition metal ions); heterobifunctional cross-linkers including, for example, monohalogenacetyl halide, epichlorohydrin as well as amino and thiol group-directed reagents. In yet a further embodiment, the reagent is cross-linked to the solid phase through a carbohydrate chain. To achieve this, the sugar moieties may be first oxidized to aldheydes which form Schiff bases with either ethylenediamine or glycyltyrosine. Sodium borohydride may be used to stabilize the bonds. The derivatized glycoprotein is immobilized to the solid phase. For a review of immobilization techniques, see Wong, S. *Chemistry of Protein Conjugation and Cross-Linking* CRC Press Inc., Boston (1991).

A "leucine zipper" is a peptide (often about 20–40 amino acid residues long) having several repeating amino acids, in which every seventh amino acid is a leucine residue. Such leucine zipper sequences form amphipathic α-helices, with the leucine residues lined up on the hydrophobic side for dimer formation. Leucine zippers may have the general structural formula known as the heptad repeat (Leucine-$X_1$-$X_2$-$X_3$,-X4-$X_5$-X6;SEQ ID NO:4)$_n$, where X may be any of the conventional 20 amino acids, but is most likely to be amino acids with tight α-helix forming potential, for example, alanine, valine, aspartic acid, glutamic acid and lysine, and n may be three or greater, although typically n is 4 or 5. Examples of leucine zippers herein include the Fos-Jun leucine zipper (O'Shea et al. *Science* 245:646 (1989)) which may be used for forming heterodimers (e.g. bispecific antibodies); the GCN4 leucine zipper from yeast (Landschulz et al. *Science* 240:1759–1764 (1988)) which may be used for forming homodimers (e.g. monospecific antibodies, as in the example below); and leucine zippers found in other DNA-binding proteins, such as C/EBP and c-myc, as well as variants of any of these.

The term "filter" when used herein refers to a porous filter media through which an aqueous phase can pass but which retains one or more contaminants. The filter can be formed from a variety of materials such as cellulose fibers, including, e.g. cellulose acetate (SARTOBIND™ membrane adsorbers by Sartorius); silica based particulate; fibrous and particulate filter elements; nylon membranes or any combination of these. The filter of interest herein is a "charged filter" (i.e. positively or negatively charged) which means that it bears an overall net positive charge or an overall net negative charge. This may be achieved, for example, by attaching "charge modifying groups" to the filter. Anionic charge modifiers include water soluble polymers having anionic functional groups such as carboxyl, phosphorous, phosphonic, sulfonic groups (U.S. Pat. No. 4,604,208). Cationic charge modifiers include melamine formaldehyde cationic colloid (U.S. Pat No. 4,007,113), inorganic cationic colloidal silica (U.S. Pat. No. 4,305,782), polyamido-polyamine epichlorohydrin cationic resin, polyamine epichlorohydrin. The filter is preferably one which allows high flow rates, without sacrificing binding capacity (as opposed to bead based columns, for example). Various configurations of the filter are contemplated, such as multilayer modules and spiral wound arrangements.

A "buffer" is a solution that resists changes in pH by the action of its acid-base conjugate components. An "equilibration buffer" is that used to prepare a solid phase for loading the polypeptide of interest. The "loading buffer" is that which is used to load the composition comprising the polypeptide and contaminants onto the solid phase. Often, the equilibration and loading buffers are the same. The "elution buffer" is used to elute the polypeptide from the solid phase.

As used herein, the term "immunoadhesin" designates antibody-like molecules which combine the "binding domain" of a heterologous "adhesin" polypeptide (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by protein A chromatography (Lindmark et al., *J. Immunol. Meth.* 62:1–13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

MODES FOR CARRYING OUT THE INVENTION

The invention herein provides a method for modifying a polypeptide and/or purifying a polypeptide from a composition comprising the polypeptide and one or more contaminants. The composition is generally one resulting from the recombinant production of the polypeptide, but may be that resulting from production of the polypeptide by peptide synthesis (or other synthetic means) or the polypeptide may be purified from a native source of the polypeptide. Preferably the polypeptide is an antibody, e.g. one which binds the CD18 antigen.

For recombinant production of the polypeptide, the nucleic acid encoding it is isolated and inserted into a replicable vector for further cloning (amplification of the DNA) or for expression. DNA encoding the polypeptide is readily isolated and sequenced using conventional procedures (e.g., where the polypeptide is an antibody by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe;* Kluyveromyces hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosbphilarum* (ATCC 36,906), *K. thermotolerans,* and *K. marxianus; yarrowia* (EP 402,226); *Pichia pastoris* (EP 183,070); Candida; *Trichoderma reesia* (EP 244,234); *Neurospora crassa;* Schwanniomyces such as *Schwanniomyces occidentalis;* and filamentous fungi such as, e.g., Neurospora, Penicillium, Tolypocladium, and Aspergillus hosts such as *A. nidulans* and *A. niger.*

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.*102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supenatants from such expression systems are generally first concentrated using a commercially available protein concentration filter, for example, an Amicon or Millipore Pellicon ultrafiltration unit.

The polypeptide is then subjected to one or more purification steps. Examples of purification procedures include fractionation on an ion-exchange column, hydrophobic interaction chromatography (e.g. on phenyl sepharose), ethanol precipitation, Reverse Phase HPLC, chromatography on silica, chromatography on heparin Sepharose™, anion exchange chromatography, cation exchange chromatography (e.g. on a Bakerbond ABX column or SP-Sepharose HP column), chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent).

In one embodiment of the invention, the recovery step involves exposing a composition comprising the polypeptide (and optionally one or more contaminants) to a solid phase to which is immobilized a reagent which binds to, or modifies, the polypeptide. This step may be at the start or end or anywhere in a sequence of recovery steps for the polypeptide. In one embodiment, the solid phase is packed in a column and the immobilized reagent captures the polypeptide. In another embodiment, the reagent chemically and/or physically modifies the polypeptide and is immobilized on the solid phase which is, e.g., packed in a column, and the composition is passed through the column. For example, the polypeptide may comprise a precursor domain which the immobilized regent removes as part of the recovery process. In the example below, the precursor polypeptide was an antibody with a leucine zipper dimerization domain which was removed by immobilized pepsin in the recovery process. Following this step, the solid phase (e.g. chromatography column) may be regenerated using techniques applicable for regenerating such a solid phase.

It has been discovered herein that leaching of the immobilized reagent from the solid phase can occur and this can result in decreased yields and/or contamination of the polypeptide preparation following this step. In particular, in the example below, it was found that the pepsin could leach from a column to which it was immobilized and result in digestion of the antibody following removal of the leucine zipper, thereby reducing yields of functional antibody.

In order to obviate this problem, the invention provides a step following exposure of the composition to the immobilized reagent as discussed above. This involves passing the composition comprising the polypeptide and leached reagent (and optionally one or more further contaminants) through a filter bearing a charge which is opposite to the charge of the reagent at the pH of the composition, so as to remove leached reagent from the composition. The filter may be positively charged to remove contaminants that are negatively charged at the pH of the composition, such as acidic proteases, protein A, protein G or other reagents that can leach from affinity columns. Alternatively, the filter may be negatively charged to remove contaminants that are positively charged at the pH of the composition, such as basic proteases. Preferably, the charge characteristics of the polypeptide of interest in the composition passed through the filter are such that the polypeptide is not significantly retained by the filter and passes therethrough. The ability of the leached reagent to bind to the filter and the polypeptide to pass through it varies depending on the pH of the composition passing though the filter. To determine which filter to use (i.e. positively or negatively charged filter), one may investigate the pI of the leached reagent and, optionally, the pI of the polypeptide exposed to the immobilized reagent as discussed above. In one embodiment (e.g. as in the example below), the pH of the composition will be such that the leached reagent and polypeptide already have opposite net charges. In another embodiment, it may be beneficial to adjust the pH of the composition to be passed through the charged filter such that the leached reagent and polypeptide have opposite charges. Such alteration of the pH of the composition may serve to increase binding of oppositely charged contaminants to the filter and/or decrease binding of the polypeptide of interest to the filter. Other modifications of the composition to achieve the same effect are envisaged herein. Following any optional modifications of the composition, a filter may be selected which has a charge opposite to that of the leached reagent to be removed from the composition.

In a preferred embodiment of the invention, the filter is placed "in line" with the effluent treated as in the previous step (i.e. the effluent flows directly though the filter). This can be achieved by connecting the filter directly to the column effluent port, before the effluent is collected into a pool tank. The filter may be regenerated using techniques applicable to the type of filter used.

The polypeptide preparation may be subjected to additional purification, if necessary. Exemplary further purification steps have been discussed above. The polypeptide thus recovered may be formulated in a pharmaceutically acceptable carrier and is used for various diagnostic, therapeutic or other uses known for such molecules.

The following examples are offered by way of illustration and not by way of limitation. The disclosures of all citations in the specification are expressly incorporated herein by reference.

EXAMPLE

This example concerns an antibody (rhuMAb CD18) produced as a precursor polypeptide with a leucine zipper domain which is removed during the purification process of the instant invention. Recombinant humanized anti-CD18 antibody (rhuMAb CD18) having the amino acid sequence shown in FIG. 1A (heavy chain; SEQ ID NO:1) and FIG. 1B (light chain; SEQ ID NO:2) was created by humanization of the murine monoclonal antibody muMAb H52 (Hildreth et al. *J. Immunology* 134:3272–3280 (1985)).

Figure 2B:
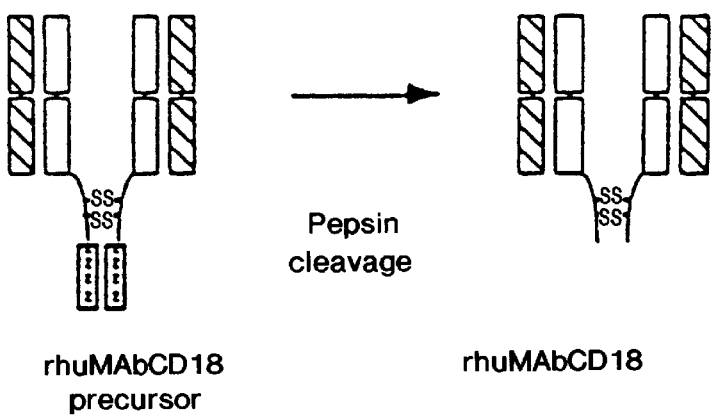

Recombinant production of rhuMAb CD18: Plasmid pS1130 was constructed to direct production of the rhuMAb CD18 precursor molecule in *E. coli*. The precursor is cleaved during the purification process by the protease pepsin to yield rhuMAb CD18. rhuMAb CD18 is an F(ab')$_2$ molecule composed of 2 different peptides (light and heavy chains) linked by disulfide bonds. The Fc region of intact antibodies normally holds the 2 Fab arms together (FIG. 2A), so when Fab' is produced in *E. coli* very little F(ab')$_2$ is formed. Fusion of a yeast GCN4 leucine zipper dimerization domain to the C-terminus of an Fab' substitutes for the Fc region and allows for efficient F(ab')$_2$ production in *E. coli*. The GCN4 leucine zipper domains interact to form stable dimeric structures (parallel coiled coils) that hold the hinge region cysteine residues of two heavy chains together so that the two native interchain disulfide bonds can form. This results in formation of F(ab')$_2$ complexes that are covalently linked by disulfide bonds. The leucine zipper domains are later removed from the rhuMAb CD18 precursor during the purification process using the protease pepsin, which cleaves uniformly between the 2 leucine residues of the hinge. This results in the formation of the rhuMAb CD18 F(ab')$_2$ molecule (FIG. 2B).

Figure 3:
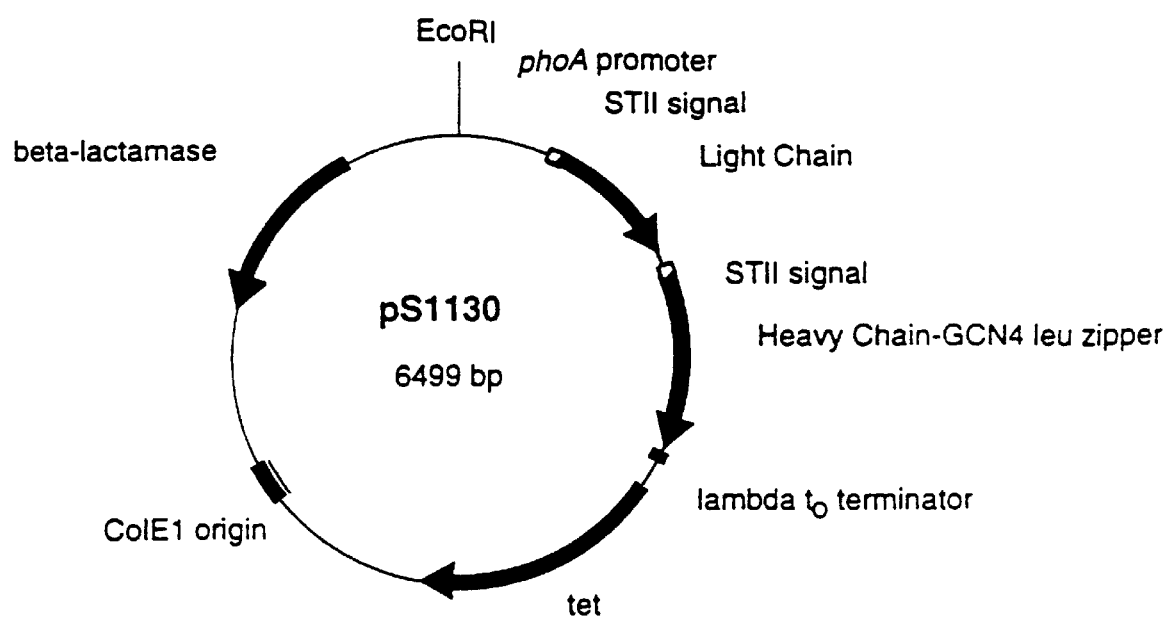
FIG. 3 depicts the structure of plasmid pS1130 used to produce rhuMAb CD18 of the example below.
Figure 6:
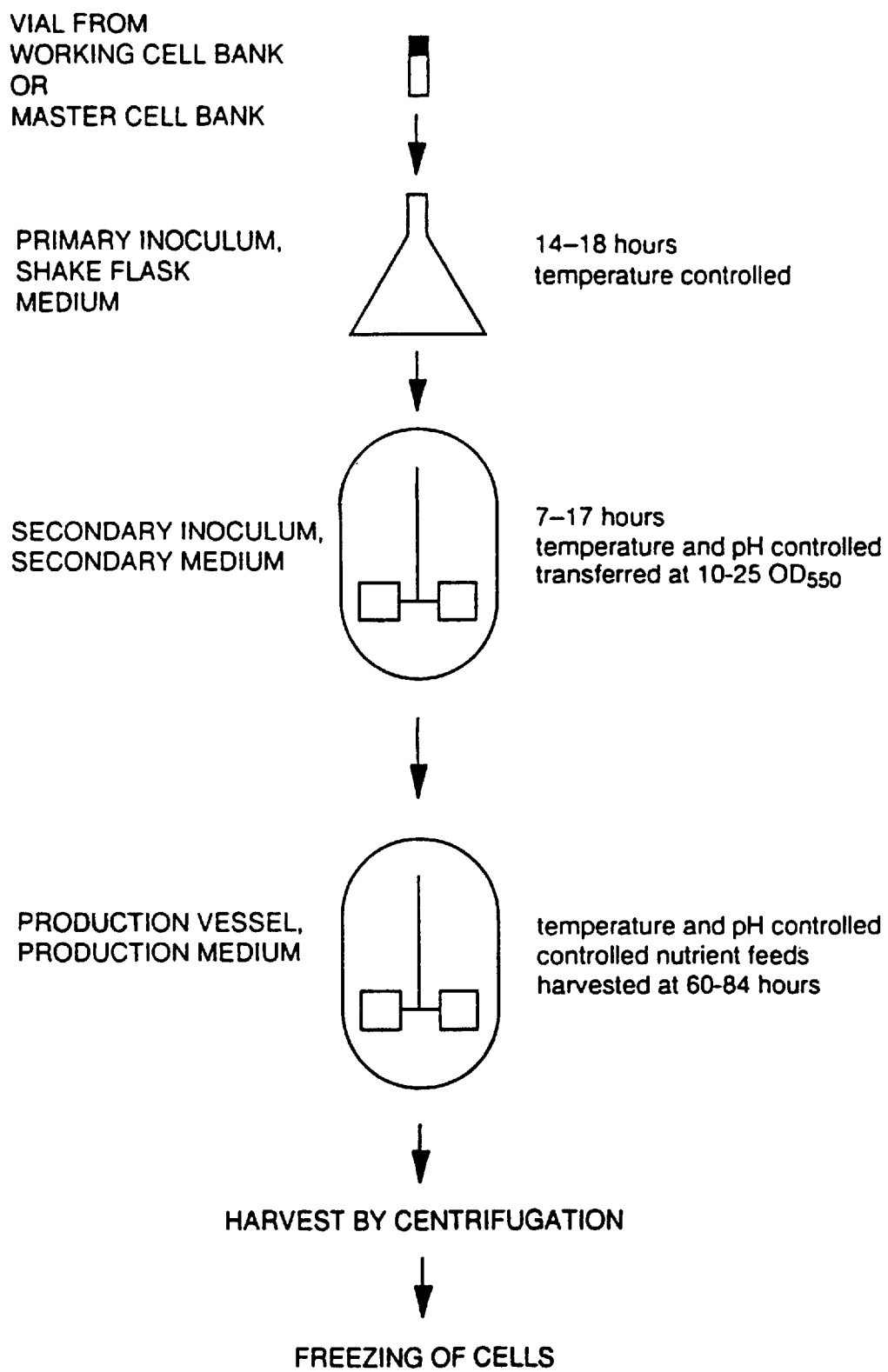
FIG. 6 is a schematic of the fermentation process for rhuMAb CD18.

Plasmid pS1130 (FIG. 3) is based on the well characterized plasmid pBR322 with a 2143 bp expression cassette (FIG. 4) inserted into the EcoRI restriction site. Plasmid pS1130 is resistant to both tetracycline and β-lactam antibiotics. The expression cassette contains a single copy of each gene linked in tandem. Transcription of each gene into a single dicistronic mRNA is directed by the *E. coli* phoA promoter (Chang et al. Gene 44:121–125 (1986)) and ends at the phage lamda $t_0$ terminator (Scholtissek and Grosse *Nucleic Acids Research* 15:3185 (1987)). Translation initiation signals for each chain are provided by *E. coli* STII (heat stable enterotoxin) (Picken et al. *Infection and Immunity* 42:269–275 (1983)) Shine-Dalgarno sequences. Translation of each chain begins with a 23 residue STII signal peptide that directs translocation of the peptides across the cytoplasmic membrane into the periplasmic space (SEQ ID NOs: 6 and 7). The STII signal peptide is then removed by the *E. coli* leader peptidase. The light and heavy chains fold into their native conformations after secretion into the periplasm and associate into the rhuMAb CD18 precursor, a covalently linked F(ab')$_2$ (FIG. 2B). The leucine zipper domain is cleaved from the precursor during the purification process (see below) to yield rhuMAb CD18 (FIG. 2B). The cell line used in the production of rhuMAb CD18 is 49A5, derived from *E. coli* cell line W3110 (ATCC 27,325) as shown in FIG. 5. The fermentation procedure takes place as shown in FIG. 6. Production of rhuMAb CD18 precursor occurs when the medium becomes depleted in phosphate, typically 30–60 hours after inoculation.

Purification of rhuMAb CD18 precursor from the *E. coli* cell paste was as follows.

Homogenization and Centrifugation: Frozen cell pellets containing anti-CD18 precursor antibody, were dissolved in about 3 volumes of extraction buffer (120 mM MES, 5 mM EDTA buffer, pH 6) heated to 30–40° C. This resulted in a suspension with a pH between about 5.4 and 6.5. This suspension was passed twice through a Gaulin homogenizer at 5500 to 6500 psi and kept below 20° C. with a heat exchanger. 5% polyethyleineimine (PEI) (w/v), pH 6 was added to the homogenate to a final concentration of 0.2% PEI. The mixture was incubated for about one hour at 2–8° C. About one volume of extraction buffer (120 mM MES, 5 mM EDTA, pH 6) was added before the solids were removed by centrifugation at 15,280 g. The clear supernatant was conditioned to a conductivity of less than 3 mohms by the addition of cold water.

Ion Exchange Chromatography: The conditioned supernatant was loaded onto a cation exchange column (ABX column; Mallinckrodt Baker, Inc., NJ, USA) equilibrated in 50 mM MES, pH 6.0. The column was washed with the equilibration buffer and the anti-CD18 precursor was eluted with a linear gradient from 50 mM MES, pH 6.0 to 50 mM MES, 100 mM sodium citrate, pH 6.0. The column was monitored by absorbance at 280 nm, and the eluate was collected in fractions. The appropriate fractions were pooled based on analytical cation exchange hydrophobic liquid chromatography (HPLC). After use, the cation exchange column was regenerated using 3.0 M guanidine HCl, 20 mM HEPES buffer, pH 7.4, followed by 1% acetic acid, 120 mM phosphoric acid. The column was stored in 1% acetic acid, 120 mM phosphoric acid.

Precursor digestion: Pepsin (Sigma, Mo., USA) was chemically coupled to controlled pore glass (CPG) by Bioprocess Ltd., UK. The CPG was activated with NaIO$_4$ followed by reduction of schiff base formation between CPG and pepsin using NaBH$_3$CN.

The cation exchange anti-CD18 precursor antibody pool of the previous step was diluted with 50 mM MES, 36 mM sodium citrate, pH 4.0 to a concentration of approximately 2 g/L. The pool was then adjusted to pH 4 by addition of 2 M citric acid and flowed through a column containing immobilized pepsin (pepsin-CPG) previously equilibrated with 50 mM MES, 36 mM sodium citrate pH 4.0. This procedure removed the zippers from the hinge region while leaving intact F(ab')$_2$. After use, the pepsin column was regenerated with 0.12% aqueous HCl, pH 1.5 and stored in 100 mM sodium acetate, 150 mM sodium chloride, 0.01% Thimerosal, 50% glycerol, pH 4.5.

Anion exchange filtration: The effluent from the pepsin-CPG column was passed directly in line through an anion exchange Sartobind Q membrane (Sartorius, Goettingen, West Germany). The generated anti-CD18 F(ab')$_2$ antibody flows through the membrane while pepsin and other negatively charge impurities bind strongly to the membrane. The membrane was regenerated using 50 mM MES, 36 mM sodium citrate, 1 M sodium chloride, pH 4.0 and was stored in 0.1 N sodium hydroxide.

Analysis of the digestion reaction: Digestion of the anti-CD18 precursor antibody was analyzed by HPLC cation-exchange chromatography on a BAKERBOND™ carboxy-sulfon (CSX) 50×4.6 mm column (J. T. Baker Phillipsburg, N.J.) maintained at 55° C. The polypeptides were eluted using an increasing linear gradient from pH 6.0 to pH 8.0 at a flow rate of 4 ml/min using a detection wavelength of 280 nm. Buffer A contained 16 mM of each HEPES/PIPES/MES, pH 6.0 and Buffer B contained 16 mM of each HEPES/PIPES/MES, pH 8.0. For the separation of digested and undigested anti-CD18 precursor antibody, a linear gradient was run for 10 min from 40% B to 100% B.

Pepsin analysis: The amount of pepsin leached from the pepsin-CPG column was determined by reverse phase HPLC analysis and by pepsin ELISA analysis.

For HPLC analysis, a TosoHass TSK-Phenyl (7.5×75 mm) column was monitored with 90% solvent A (0.1% TFA in water) and 10% solvent B (0.1% TFA in acetonitrile). Upon 75 μg sample injection, a 30 minute gradient from 10% to 25% solvent B was initiated; the flow rate was 1 ml/min, and the temperature was maintained at 55° C. throughout.

For the ELISA, a sandwich ELISA was performed. Polyclonal goat anti-pepsin antibodies were used to coat a 96-well microtiter plate. Pepsin containing samples and standards were incubated in the coated wells. The sandwich was completed with biotinylated-goat-anti-pepsin. Prior to biotinylation, the second antibodies were affinity purified using CPG-pepsin. The immunological complexes were detected in the plates using streptavidin-alkaline phosphatase and p-nitrophenyl phosphate substrate. Absorbance at 405 nm was measured in a microtiter plate reader. Standards cover the range of 33.3 μg/ml down to 0.5 μg/ml in 2-fold dilutions. Dilutions were made for the samples (pure sample or diluted 1:2, 1:4, and 1:8). Samples were also spiked at the level of 10 μg/ml with pepsin and assayed as samples. The detection limit of the assay was 1 μg/ml. A 4-parameter logistic curve fit to the data produced an acceptable standard curve.

Cation exchange chromatography: The pool was diluted to give a conductivity of approx. 7 mohms by the addition of water. The pool was applied to a cation exchange column (SP Sepharose High Performance; SPHP) equilibrated in 25 mM MES, 60 mM acetic acid, pH 4.0. The SP Sepharose column was washed with 25 mM MES, 75 mM sodium acetate pH 5.6 and eluted in a linear gradient of 75–110 mM sodium acetate in 25 mM MES pH 5.6. The column eluate was monitored at 280 nm and the eluate fractions were pooled based on analytical ion exchange HPLC. The SP Sepharose column was regenerated in 25 mM MES, 400 mM sodium acetate pH 5.6 followed by a wash with 0.5% sodium hydroxide. The column was stored in 0.1% NaOH.

Hydrophobic Interaction Chromatography (HIC): The pooled fraction from the SP sepharose column was diluted with the addition of 3.0M ammonium sulphate, 25 mM MES pH 6.0 at a ratio of 0.26 liters per liter of pool. This was then passed through a HIC column (phenyl sepharose FF—low substitution) previously equilibrated in 0.625 M ammonium sulphate, 25 mM MES pH 6.0. After loading, the column was washed with the same buffer used in the equilibration and the rhuMAb CD18 eluted in 0.375M ammonium sulphate, 25 mM MES pH 6.0. The eluate was monitored at 280 nm and the fractions are collected based on analytical reversed phase HPLC. The HIC column was regenerated in 25 mM MES, pH 6.0, followed by a wash in 0.5% NaOH. The column was stored in 0.1% NaOH.

RESULTS

Figure 7:
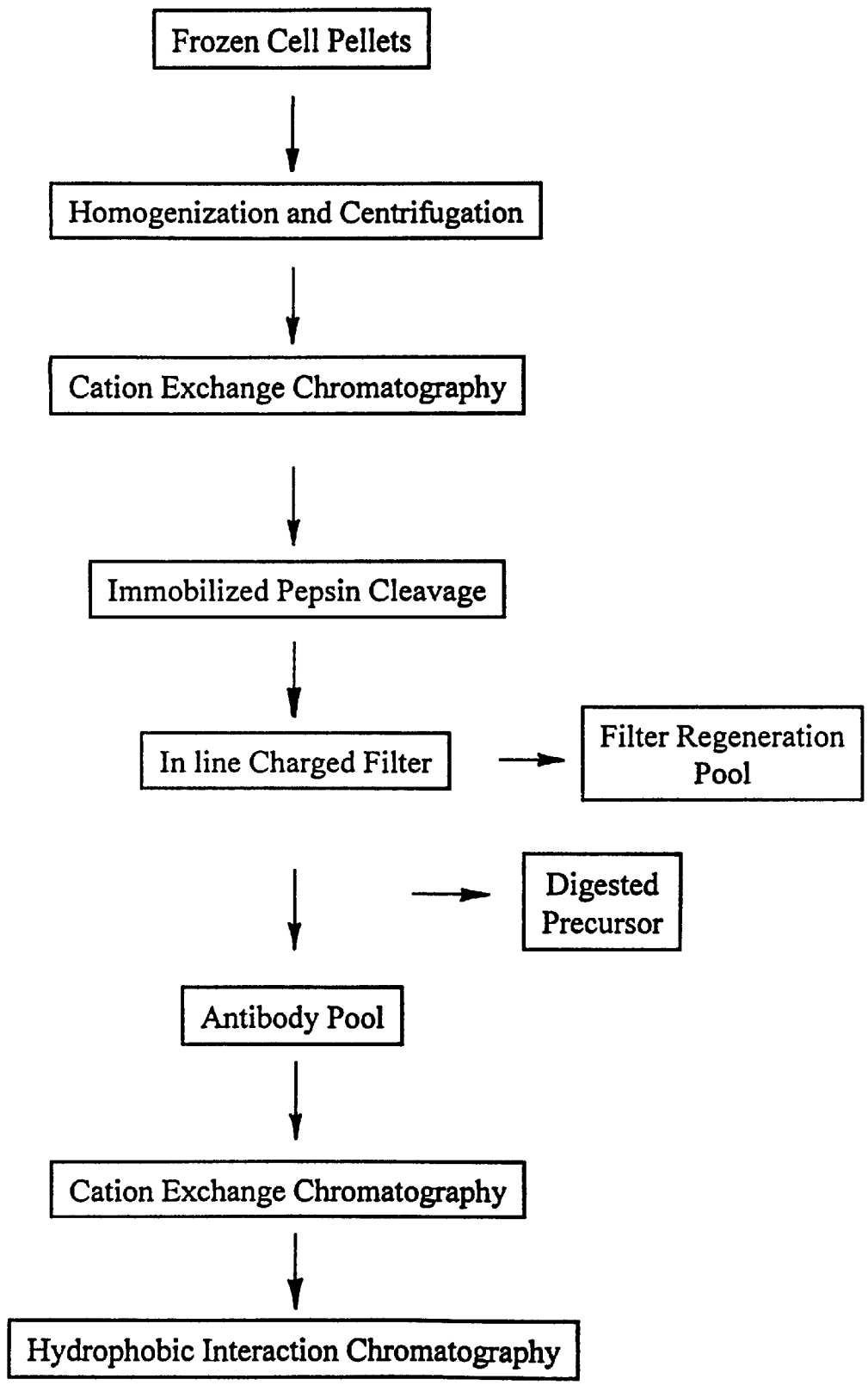
FIG. 7 is a flow diagram depicting the purification steps for rhuMAb CD18.

Two separate large scale purification runs were performed (see FIG. 7). The purification process started with *E. coli* cell paste containing anti-CD18 precursor antibody, and completed with the anti-CD18 F(ab')$_2$ lacking the leucine zipper dimerization domain. During both purification runs, digestion of the antibody precursor molecule was performed by passing partially purified anti-CD18 precursor antibody through a pepsin-CPG column. Digestion was monitored by SDS PAGE and analytical cation exchange HPLC. The total amount of pepsin leached from the pepsin-CPG column was determined by measuring pepsin in the digested precursor antibody pool after the CPG-pepsin digestion and filtration step and in the anion exchange membrane regeneration pool. Regeneration of the membrane was performed by eluting pepsin and contaminants attached to the membrane using 50 mM MES, 36 mM sodium citrate, 1 M sodium chloride, buffer pH 4.0 (see FIG. 7). The effective removal of pepsin throughout the purification steps was monitored by Western blots using purified goat anti-pepsin antibodies and quantitated using the ELISA method.

The results of the reverse phase HPLC analysis are shown in Table 1. In the first run, pepsin was detected in both the anion exchange membrane regeneration pool at a concentration of 40 μg/ml and in the digested precursor antibody pool after the CPG-pepsin and filtration step at a concentration of 48.3 μg/ml. By adding the total concentration of pepsin in both pools it was determined that 13.4 g of pepsin leached from the CPG-pepsin column during the digestion step in the first run. The data also revealed that the amount of filtration area used to remove leached pepsin was not enough at the flow rates and pH used in the first run. Nevertheless, the membrane was able to remove 21% of the total amount of pepsin leached from the pepsin-CPG column. Since the digested precursor antibody pool contained 10.6 g of leached pepsin that was not removed by the membrane, the purification yields from the pepsin-CPG digestion step and the SPHP step were low; 77 and 53%, respectively. Also, pepsin was detected in the SPHP pool by Western blot analysis.

TABLE 1

|  | Pepsin concentration |
|---|---|
| RUN #1 | |
| Pepsin digested Ab pool | 48.3 μg/ml |
| Pepsin digested Ab pool volume | 220 L |
| Total amount of pepsin Ab pool | 10.6 g |
| Membrane regeneration pool | 40.4 μg/ml |
| Membrane regeneration volume | 70 L |
| Total amount of pepsin Membrane pool | 2.8 g |
| RUN #2 | |
| Pepsin digested Ab pool | 0 |
| Pepsin digested Ab pool volume | 630 L |
| Total amount of pepsin Ab pool | 0 |
| Membrane regeneration pool | 230 μg/ml |
| Membrane regeneration volume | 10 L |
| Total amount of pepsin Membrane pool | 2.3 g |

After the final purification step (Phenyl sepharose), pepsin was not detected by ELISA (Table 2) or by Western blot analysis. In the second run, the filtration area of the anion exchange membrane was doubled from 11,000 cm$^2$ to 22,000 cm$^2$. Pepsin was detected only in the anion exchange regeneration pool at a concentration of 230 μg/ml. Pepsin was not detected in the digested precursor antibody pool, after the CPG-pepsin digestion and filtration steps. The total amount of pepsin leached by the CPG-pepsin resin was 2.3 g. This value is 17% of the total amount of leached pepsin detected during the first run. Pepsin was not detected by reverse phase, pepsin ELISA or Western blots through the remaining purification steps of the second run. As a result of completely removing pepsin from the digested precursor pool, the purification yields from the pepsin-CPG digestion step and the SPHP were improved to 97 and 90%, respectively.

TABLE 2

| Sample | Pepsin Values (mean of 2 reps.) [μg/ml] |
|---|---|
| Abx pool | <.5, <.5 |
| Q pool run 1 | 7.4 |
| Q pool run2 | <.5, <.5 |
| SPHP Pool run 1 | <.5, <.5 |
| SPHP Pool run 2 | <.5, <.5 |
| HIC pool run 1 | <.5, <.5 |
| HIC pool run 2 | <.5, <.5 |
| Form. product run 1 | <.5, <.5 |
| Form. product run 2 | <.5, <.5 |
| Placebo formulation | <.5, <.5 |

The results of these experiments demonstrate that the use of a positively charged membrane in line immediately after the immobilized pepsin digestion step was advantageous. When pepsin was not completely removed by the membrane from the digested precursor antibody pool, decreased yields of functional antibody were obtained. Without being bound to any one theory, this was probably the result of overdigestion by the remaining pepsin in the pool. Furthermore when pepsin is not completely removed by the positively charged membrane it was detected in the SPHP pool by Western blots. In the second run, leached pepsin was completely removed by the membrane. As a result the recovery yields for the pepsin digestion step and the SPHP cation exchange steps improved. Introduction of the anion exchange membrane improved the anti-CD18 purification process in two fundamental ways. First yields were improved by effectively removing pepsin from the CPG digestion pool, preventing further digestion. Second the overall efficiency and reproducibility of the process was improved by removing pepsin and other negatively charged contaminants early in the process.

What is claimed is:

1. A method for modifying a precursor antibody comprising a leucine zipper comprising exposing the precursor antibody to a protease immobilized on a solid phase such that the protease removes the leucine zipper from the precursor antibody.

2. The method of claim 1 further comprising passing the antibody from which the leucine zipper has been removed through a positively charged filter.

3. The method of claim 1 wherein the protease is pepsin.

4. The method of claim 1 wherein the solid phase comprises controlled pore glass beads.

5. The method of claim 1 wherein the antibody is a F(ab')$_2$.

6. The method of claim 1 wherein the leucine zipper is GCN4.

7. The method of claim 1 wherein the antibody binds CD18.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 241 amino acids
      (B) TYPE: Amino Acid
      (D) TOPOLOGY: Linear (xi) SEQUENCE DESCRIPTION: SEQ ID NO: 1:

```
Glu Val Gln Leu Val Glu Ser Gly Gly Gly Leu Val Gln Pro Gly
 1               5                  10                  15

Gly Ser Leu Arg Leu Ser Cys Ala Thr Ser Gly Tyr Thr Phe Thr
                20                  25                  30

Glu Tyr Thr Met His Trp Met Arg Gln Ala Pro Gly Lys Gly Leu
                35                  40                  45

Glu Trp Val Ala Gly Ile Asn Pro Lys Asn Gly Gly Thr Ser His
                50                  55                  60

Asn Gln Arg Phe Met Asp Arg Phe Thr Ile Ser Val Asp Lys Ser
                65                  70                  75

Thr Ser Thr Ala Tyr Met Gln Met Asn Ser Leu Arg Ala Glu Asp
                80                  85                  90

Thr Ala Val Tyr Tyr Cys Ala Arg Trp Arg Gly Leu Asn Tyr Gly
                95                 100                 105

Phe Asp Val Arg Tyr Phe Asp Val Trp Gly Gln Gly Thr Leu Val
               110                 115                 120

Thr Val Ser Ser Ala Ser Thr Lys Gly Pro Ser Val Phe Pro Leu
               125                 130                 135

Ala Pro Ser Ser Lys Ser Thr Ser Gly Gly Thr Ala Ala Leu Gly
               140                 145                 150

Cys Leu Val Lys Asp Tyr Phe Pro Glu Pro Val Thr Val Ser Trp
               155                 160                 165

Asn Ser Gly Ala Leu Thr Ser Gly Val His Thr Phe Pro Ala Val
               170                 175                 180

Leu Gln Ser Ser Gly Leu Tyr Ser Leu Ser Ser Val Val Thr Val
               185                 190                 195

Pro Ser Ser Ser Leu Gly Thr Gln Thr Tyr Ile Cys Asn Val Asn
               200                 205                 210

His Lys Pro Ser Asn Thr Lys Val Asp Lys Lys Val Glu Pro Lys
               215                 220                 225

Ser Cys Asp Lys Thr His Thr Cys Pro Pro Cys Pro Ala Pro Glu
               230                 235                 240

Leu
241
```

(2) INFORMATION FOR SEQ ID NO: 2:

(i) SEQUENCE CHARACTERISTICS:
        (A) LENGTH: 214 amino acids
        (B) TYPE: Amino Acid
        (D) TOPOLOGY: Linear (xi) SEQUENCE DESCRIPTION: SEQ ID NO: 2:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Asn
                20                  25                  30

Asn Tyr Leu Asn Trp Tyr Gln Gln Lys Pro Gly Lys Ala Pro Lys
                35                  40                  45

Leu Leu Ile Tyr Tyr Thr Ser Thr Leu His Ser Gly Val Pro Ser
                50                  55                  60

Arg Phe Ser Gly Ser Gly Ser Gly Thr Asp Tyr Thr Leu Thr Ile
                65                  70                  75

Ser Ser Leu Gln Pro Glu Asp Phe Ala Thr Tyr Tyr Cys Gln Gln
                80                  85                  90

Gly Asn Thr Leu Pro Pro Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys
               214

(2) INFORMATION FOR SEQ ID NO: 3:

(i) SEQUENCE CHARACTERISTICS:
        (A) LENGTH: 36 amino acids
        (B) TYPE: Amino Acid
        (D) TOPOLOGY: Linear (xi) SEQUENCE DESCRIPTION: SEQ ID NO: 3:

Leu Gly Gly Arg Met Lys Gln Leu Glu Asp Lys Val Glu Glu Leu
 1               5                  10                  15

Leu Ser Lys Asn Tyr His Leu Glu Asn Glu Val Ala Arg Leu Lys
                20                  25                  30

Lys Leu Val Gly Glu Arg
                35  36

(2) INFORMATION FOR SEQ ID NO: 4:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 4:

Leu Xaa Xaa Xaa Xaa Xaa Xaa
 1           5       7

(2) INFORMATION FOR SEQ ID NO: 5:

(i) SEQUENCE CHARACTERISTICS:
        (A) LENGTH: 2143 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

```
GAATTCAACT TCTCCATACT TTGGATAAGG AAATACAGAC ATGAAAAATC          50

TCATTGCTGA GTTGTTATTT AAGCTTTGGA GATTATCGTC ACTGCAATGC         100

TTCGCAATAT GGCGCAAAAT GACCAACAGC GGTTGATTGA TCAGGTAGAG         150

GGGGCGCTGT ACGAGGTAAA GCCCGATGCC AGCATTCCTG ACGACGATAC         200

GGAGCTGCTG CGCGATTACG TAAAGAAGTT ATTGAAGCAT CCTCGTCAGT         250

AAAAAGTTAA TCTTTTCAAC AGCTGTCATA AAGTTGTCAC GGCCGAGACT         300

TATAGTCGCT TTGTTTTTAT TTTTTAATGT ATTTGTAACT AGAATTCGAG         350

CTCGCCGGGG ATCCTCTAGA GGTTGAGGTG ATTTTATGAA AAAGAATATC         400

GCATTTCTTC TTGCATCTAT GTTCGTTTTT TCTATTGCTA CAAACGCGTA         450

CGCTGATATC CAGATGACCC AGTCCCCGAG CTCCCTGTCC GCCTCTGTGG         500

GCGATAGGGT CACCATCACC TGTCGTGCCA GTCAGGACAT CAACAATTAT         550

CTGAACTGGT ATCAACAGAA ACCAGGAAAA GCTCCGAAAC TACTGATTTA         600

CTATACCTCC ACCCTCCACT CTGGAGTCCC TTCTCGCTTC TCTGGTTCTG         650

GTTCTGGGAC GGATTACACT CTGACCATCA GCAGTCTGCA ACCGGAGGAC         700

TTCGCAACTT ATTACTGTCA GCAAGGTAAT ACTCTGCCGC CGACGTTCGG         750

ACAGGGCACG AAGGTGGAGA TCAAACGAAC TGTGGCTGCA CCATCTGTCT         800

TCATCTTCCC GCCATCTGAT GAGCAGTTGA AATCTGGAAC TGCCTCTGTT         850

GTGTGCCTGC TGAATAACTT CTATCCCAGA GAGGCCAAAG TACAGTGGAA         900

GGTGGATAAC GCCCTCCAAT CGGGTAACTC CCAGGAGAGT GTCACAGAGC         950

AGGACAGCAA GGACAGCACC TACAGCCTCA GCAGCACCCT GACGCTGAGC        1000

AAAGCAGACT ACGAGAAACA CAAAGTCTAC GCCTGCGAAG TCACCCATCA        1050

GGGCCTGAGC TCGCCCGTCA CAAAGAGCTT CAACAGGGGA GAGTGTTAAG        1100

CTGATCCTCT ACGCCGGACG CATCGTGGCG CTAGTACGCA AGTTCACGTA        1150

AAAACGGTAT CTAGAGGTTG AGGTGATTTT ATGAAAAAGA ATATCGCATT        1200

TCTTCTTGCA TCTATGTTCG TTTTTTCTAT TGCTACAAAC GCGTACGCTG        1250

AGGTTCAGCT GGTGGAGTCT GGCGGTGGCC TGGTGCAGCC AGGGGGCTCA        1300

CTCCGTTTGT CCTGTGCAAC TTCTGGCTAC ACCTTTACCG AATACACTAT        1350

GCACTGGATG CGTCAGGCCC CGGGTAAGGG CCTGGAATGG GTTGCAGGGA        1400

TTAATCCTAA AAACGGTGGT ACCAGCCACA ACCAGAGGTT CATGGACCGT        1450

TTCACTATAA GCGTAGATAA ATCCACCAGT ACAGCCTACA TGCAAATGAA        1500

CAGCCTGCGT GCTGAGGACA CTGCCGTCTA TTATTGTGCT AGATGGCGAG        1550
```

```
GCCTGAACTA CGGCTTTGAC GTCCGTTATT TTGACGTCTG GGGTCAAGGA        1600

ACCCTGGTCA CCGTCTCCTC GGCCTCCACC AAGGGCCCAT CGGTCTTCCC        1650

CCTGGCACCC TCCTCCAAGA GCACCTCTGG GGGCACAGCG GCCCTGGGCT        1700

GCCTGGTCAA GGACTACTTC CCCGAACCGG TGACGGTGTC GTGGAACTCA        1750

GGCGCCCTGA CCAGCGGCGT GCACACCTTC CCGGCTGTCC TACAGTCCTC        1800

AGGACTCTAC TCCCTCAGCA GCGTGGTGAC CGTGCCCTCC AGCAGCTTGG        1850

GCACCCAGAC CTACATCTGC AACGTGAATC ACAAGCCCAG CAACACCAAG        1900

GTCGACAAGA AAGTTGAGCC CAAATCTTGT GACAAAACTC ACACATGCCC        1950

GCCGTGCCCA GCACCAGAAC TGCTGGGCGG CCGCATGAAA CAGCTAGAGG        2000

ACAAGGTCGA AGAGCTACTC TCCAAGAACT ACCACCTAGA GAATGAAGTG        2050

GCAAGACTCA AAAAGCTTGT CGGGGAGCGC TAAGCATGCG ACGGCCCTAG        2100

AGTCCCTAAC GCTCGGTTGC CGCCGGGCGT TTTTTATTGT TAA              2143
```

(2) INFORMATION FOR SEQ ID NO: 6:

(i) SEQUENCE CHARACTERISTICS:
        (A) LENGTH: 237 amino acids
        (B) TYPE: Amino Acid
        (D) TOPOLOGY: Linear (xi) SEQUENCE DESCRIPTION: SEQ ID NO: 6:

```
Met Lys Lys Asn Ile Ala Phe Leu Leu Ala Ser Met Phe Val Phe
-23         -20                 -15                 -10

Ser Ile Ala Thr Asn Ala Tyr Ala Asp Ile Gln Met Thr Gln Ser
            -5                  1                   5

Pro Ser Ser Leu Ser Ala Ser Val Gly Asp Arg Val Thr Ile Thr
        10                  15                  20

Cys Arg Ala Ser Gln Asp Ile Asn Asn Tyr Leu Asn Trp Tyr Gln
        25                  30                  35

Gln Lys Pro Gly Lys Ala Pro Lys Leu Leu Ile Tyr Tyr Thr Ser
        40                  45                  50

Thr Leu His Ser Gly Val Pro Ser Arg Phe Ser Gly Ser Gly Ser
        55                  60                  65

Gly Thr Asp Tyr Thr Leu Thr Ile Ser Ser Leu Gln Pro Glu Asp
        70                  75                  80

Phe Ala Thr Tyr Tyr Cys Gln Gln Gly Asn Thr Leu Pro Pro Thr
        85                  90                  95

Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly
        145                 150                 155

Asn Ser Gln Glu Ser Val Thr Glu Gln Asp Ser Lys Asp Ser Thr
        160                 165                 170

Tyr Ser Leu Ser Ser Thr Leu Thr Leu Ser Lys Ala Asp Tyr Glu
        175                 180                 185

Lys His Lys Val Tyr Ala Cys Glu Val Thr His Gln Gly Leu Ser
        190                 195                 200
```

```
Ser Pro Val Thr Lys Ser Phe Asn Arg Gly Glu Cys
        205                 210             214
```

(2) INFORMATION FOR SEQ ID NO: 7:

(i) SEQUENCE CHARACTERISTICS:
        (A) LENGTH: 300 amino acids
        (B) TYPE: Amino Acid
        (D) TOPOLOGY: Linear (xi) SEQUENCE DESCRIPTION: SEQ ID NO: 7:

```
Met Lys Lys Asn Ile Ala Phe Leu Leu Ala Ser Met Phe Val Phe
-23         -20             -15                 -10

Ser Ile Ala Thr Asn Ala Tyr Ala Glu Val Gln Leu Val Glu Ser
            -5              1               5

Gly Gly Gly Leu Val Gln Pro Gly Gly Ser Leu Arg Leu Ser Cys
        10              15              20

Ala Thr Ser Gly Tyr Thr Phe Thr Glu Tyr Thr Met His Trp Met
        25              30              35

Arg Gln Ala Pro Gly Lys Gly Leu Glu Trp Val Ala Gly Ile Asn
        40              45              50

Pro Lys Asn Gly Gly Thr Ser His Asn Gln Arg Phe Met Asp Arg
        55              60              65

Phe Thr Ile Ser Val Asp Lys Ser Thr Ser Thr Ala Tyr Met Gln
        70              75              80

Met Asn Ser Leu Arg Ala Glu Asp Thr Ala Val Tyr Tyr Cys Ala
        85              90              95

Arg Trp Arg Gly Leu Asn Tyr Gly Phe Asp Val Arg Tyr Phe Asp
        100             105             110

Val Trp Gly Gln Gly Thr Leu Val Thr Val Ser Ser Ala Ser Thr
        115             120             125

Lys Gly Pro Ser Val Phe Pro Leu Ala Pro Ser Ser Lys Ser Thr
        130             135             140

Ser Gly Gly Thr Ala Ala Leu Gly Cys Leu Val Lys Asp Tyr Phe
        145             150             155

Pro Glu Pro Val Thr Val Ser Trp Asn Ser Gly Ala Leu Thr Ser
        160             165             170

Gly Val His Thr Phe Pro Ala Val Leu Gln Ser Ser Gly Leu Tyr
        175             180             185

Ser Leu Ser Ser Val Val Thr Val Pro Ser Ser Ser Leu Gly Thr
        190             195             200

Gln Thr Tyr Ile Cys Asn Val Asn His Lys Pro Ser Asn Thr Lys
        205             210             215

Val Asp Lys Lys Val Glu Pro Lys Ser Cys Asp Lys Thr His Thr
        220             225             230

Cys Pro Pro Cys Pro Ala Pro Glu Leu Leu Gly Gly Arg Met Lys
        235             240             245

Gln Leu Glu Asp Lys Val Glu Glu Leu Leu Ser Lys Asn Tyr His
        250             255             260

Leu Glu Asn Glu Val Ala Arg Leu Lys Lys Leu Val Gly Glu Arg
        265             270             275     277
```